United States Patent [19]

Francis

[11] 4,083,972

[45] Apr. 11, 1978

[54] COMPOSITIONS FOR INHIBITING ANOMALOUS DEPOSITION AND MOBILIZATION OF CALCIUM PHOSPHATE IN ANIMAL TISSUE

[75] Inventor: Marion David Francis, Cincinnati, Ohio

[73] Assignee: The Procter & Gamble Company, Cincinnati, Ohio

[21] Appl. No.: 714,547

[22] Filed: Aug. 16, 1976

Related U.S. Application Data

[63] Continuation of Ser. No. 371,440, Jun. 19, 1973, abandoned.

[51] Int. Cl.² ........................................... A61K 31/66
[52] U.S. Cl. ................................................ 424/204
[58] Field of Search ...................................... 424/204

[56] References Cited

U.S. PATENT DOCUMENTS

| | | | |
|---|---|---|---|
| 3,488,419 | 1/1970 | McCune et al. | 424/49 |
| 3,497,313 | 2/1970 | Quimby | 23/50 |
| 3,536,628 | 10/1970 | Lancashire | 252/117 |
| 3,560,608 | 2/1971 | Griebstein et al. | 424/49 |
| 3,641,246 | 2/1972 | Francis | 424/204 |
| 3,662,066 | 5/1972 | Francis | 424/204 |
| 3,719,756 | 3/1973 | Francis | 424/204 |

OTHER PUBLICATIONS

Fleisch et al., Europ. J. Clinical Invest., vol. 1, pp. 12–18, (1970).

*Primary Examiner*—Stanley J. Friedman
*Attorney, Agent, or Firm*—Jerry J. Yetter; Julius P. Filcik; Richard C. Witte

[57] ABSTRACT

Compositions for inhibiting anomalous deposition and mobilization of calcium phosphates in animal tissue, comprising an effective amount of an alkali metal, ammonium or substituted ammonium carbonyldiphosphonate in a pharmaceutical carrier; and a method for treating conditions involving pathological calcification and hard tissue demineralization in an animal comprising administering to such animal said compositions.

2 Claims, No Drawings

COMPOSITIONS FOR INHIBITING ANOMALOUS DEPOSITION AND MOBILIZATION OF CALCIUM PHOSPHATE IN ANIMAL TISSUE

This is a continuation of application Ser. No. 371,440, filed June 19, 1973, now abandoned.

BACKGROUND OF THE INVENTION

This invention relates to novel compositions having therapeutic and/or prophylactic effects. The invention further relates to a novel method for treating or preventing certain pathological conditions in animals.

A number of pathological conditions which can afflict warm-blooded animals involve abnormal calcium and phosphate metabolism. Such conditions may be divided into two broad categories.

(1) Conditions which are characterized by anomalous mobilization of calcium and phosphate leading to general or specific bone loss or excessively high calcium and phosphate levels in the fluids of the body. Such conditions are sometimes referred to herein as pathological hard tissue demineralizations.

(2) Conditions which cause or result from deposition of calcium and phosphate anomalously in the body. These conditions are sometimes referred to herein as pathological calcifications.

The first category includes osteoporosis a condition in which bone hard tissue is lost disproportionately to the development of new hard tissue. Marrow and blood spaces become larger, fibrous binding decreases, and compact bone becomes cancellous and fragile. Osteoporosis can be subclassified as menopausal, senile, drug induced (e.g., adrenocorticoid as can occur in steroid therapy), disease induced (e.g., arthritic and tumor), etc., however, the manifestations are essentially the same. Another condition in the first category is Paget's disease (osteitis deformans) which is also characterized by bone loss. In this disease, dissolution of normal bone occurs which is then replaced by soft, poorly mineralized tissue such that the bone becomes deformed from pressures of weight bearing, particularly in the tibia and femur. This condition also frequently sponsors pathological deposition of calcium and phosphate.

The second category, involving conditions manifested by anomalous calcium and phosphate deposition, includes such afflictions as arthritis, neuritis, bursitis, tendinitis and other inflammatory conditions which predispose involved tissue to deposition of calcium phosphates, and hormonal imbalance, e.g., hyperparathyroidism, myositis ossificans progressiva, calcinosis universalis, resulting in calcification of soft tissues. Atherosclerosis is another condition in this category and involves degeneration and proliferate change in the intima which produces fibrous, lipoid plaques. If such plaques calcify, or if the inner walls of the arteries accumulate plaque and calcify, this condition is commonly referred to as arteriosclerosis.

Yet another condition in category (2) which results from anomalous calcium and phosphate deposition is stone or calculi formation in the bile duct, gall bladder, pancreas, salivary glands, tonsils, kidneys and bladder. Although some of such stones are not comprised primarily of calcium phosphate, it is likely that the original nidus is calcium phosphate. The formation of urinary calculi, i.e., urolithiasis, in cattle and sheep constitutes a major problem in veterinary medicine. It is estimated that from 5 to 10% of weanling calves suffer this affliction when they are taken off milk and start taking in other fluids.

As far as is known, no satisfactory medical treatment for the conditions of category (1) as described above has been developed prior to this invention although dietary control, fluorides, chelators such as EDTA, and the hormone calcitonin (thyrocalcitonin) have been suggested or used for these conditions. Although certain inorganic phosphates such as pyrophosphates and longer chain condensed phosphates have been suggested for treatment of conditions in category (2), they have not been widely used because of their tendency to hydrolyze to the ineffective orthophosphate when administered to larger animals such as humans and cattle.

Various organic polyphosphonates have been shown to be effective in inhibiting anomalous deposition and mobilization of calcium phosphate as is disclosed in the copending application of Marion D. Francis, Ser. No. 775,203, filed Nov. 12, 1968; however, researchers continue to seek effective alternatives.

It is therefore an object of this invention to provide a composition for inhibiting anomalous deposition and mobilization of calcium phosphate in animal tissue.

It is a further object of this invention to provide an improved method for treatment of conditions involving pathological calcification and hard tissue demineralization in animals.

SUMMARY OF THE INVENTION

This invention is based on the discovery that carbonyldiphosphonates (as hereinafter defined) reduce anomalous mobilization and deposition of calcium phosphates in animals. The invention thus involves a composition and method for treating conditions involving pathological demineralization of bony tissue and pathological calcium deposition in the soft tissue of animals. In its method aspect, the invention comprises administering to said animals an effective amount of a carbonyldiphosphonate as hereinafter characterized.

DETAILED DESCRIPTION OF THE INVENTION

In one of its aspects, this invention is a composition comprising an effective but non-toxic amount of carbonyldiphosphonate having the structural formula:

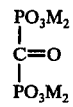

wherein each M represents alkali metal, ammonium or low molecular weight substituted ammonium and a pharmaceutical carrier.

Examples of salts suitable for use herein are the sodium, potassium, ammonium and low-molecular weight substituted ammonium (e.g., mono-, di-, and triethanolammonium) carbonyldiphosphonates. Preferred for use in the compositions and method of this invention are the sodium carbonyldiphosphonates.

The carbonyldiphosphonates can be prepared by any suitable method, however, an especially preferred method is disclosed by Oscar T. Quimby, U.S. Pat. No. 3,497,313, granted Feb. 24, 1970. The use of these compounds as anticalculus agents in oral compositions is disclosed and claimed in the concurrently filed application of Marion D. Francis, Ser. No. 51,356, filed June 30, 1970.

The required dosage of carbonyldiphosphonate will vary with the particular condition being treated, the severity of the condition, and the duration of treatment; however, single dosages can range from 0.01 to 500 mg. per kilogram of body weight, preferably 0.1 to 50 mg./kg., with up to four dosages daily. The higher dosages within this range are, of course, required in the case of oral administration because of limited absorption. Dosages greater than about 500 mg./kg. may produce toxic symptoms and should be avoided. Moreover, daily dosages greater than about 2000 mg./kg. (unless otherwise specified, the unit designated "mg./kg." as used herein refers to mg. of compound/kg. of body weight) are not required to produce the desired effect and may produce toxic side effects. Dosages of less than about .01 mg./kg. do not materially affect pathological calcification or demineralization, even administered intravenously. Table 1 below sets forth preferred dosages for various conditions which can be treated in accordance with this invention.

TABLE I

| Condition | Oral Dosage (mg./kg.) Up to Four Times/Day |
|---|---|
| Osteoporosis (menopausal)* | 1-25 |
| Osteoporosis (senile, et al.) | 1-25 |
| Paget's Disease | 5-50 |
| Arthritis | 1-25 |
| Bursitis | 1-25 |
| Neuritis | 1-25 |
| Stones | 1-25 |

*A larger initial dosage may be required, e.g., up to 500 mg./kg. followed by the specified dosage level.

The carbonyldiphosphonates can also be administered parenterally in aqueous solution by subcutaneous, intradermal, intramuscular, intraperitoneal, or intravenous injection. The preferred single dosage ranges by these modes of administration are as follows:

Subcutaneous: 0.1 – 10 mg./kg.
Intradermal: 0.1 – 10 mg./kg.
Intramuscular: 0.05 – 5 mg./kg.
Intravenous: 0.05 – 5 mg./kg.
Intraperitoneal: 0.05 – 5 mg./kg.

For purposes of oral administration, the carbonyldiphosphonates can be formulated in the form of capsules, tablets or granules. For treatment of non-human animals, the carbonyldiphosphonates are preferably incorporated in animal feed, feed supplements or feed concentrates. They can also be prepared in unit dosage from together with a pharmaceutical carrier, each unit dosage form containing from 15 mg. to 10 g. of carbonyldiphosphonate. The preferred concentration range of carbonyldiphosphonate in unit dosage forms intended for use by humans and smaller domesticated animals is from 15 mg. to 1000 mg., more preferably 100 mg. to 500 mg. A higher concentration range, i.e., from 1 g. to 5 g., is preferred in unit dosage forms intended for treatment of larger animals such as cattle, horses, etc.

When administered orally, the compositions of this invention are preferably in a form adapted to minimal exposure of the carbonyldiphosphonates to the oral cavity. Although these compounds do not damage dental enamel when applied to the tooth surfaces at the relatively low concentrations typical of toothpaste, mouthwash, lozenges and the like intended for dental calculus prophylaxis, the substantially higher concentrations of carbonyldiphosphonates provided in the unit dosage form embodiments of this invention may demineralize dental enamel on repeated prolonged exposure. Thus, oral administration is preferably effected with such unit dosage forms as capsules, pills, and tablets which are promptly ingested. Troches, chewable tablets and the like which typically remain in the oral cavity for a substantial time prior to ingestion are preferably avoided.

As used herein, the term "pharmaceutical carrier" denotes a solid or liquid filler, diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents and preservatives, can also be present.

The pharmaceutical carrier employed in conjunction with the carbonyldiphosphonates is used at a concentration sufficient to provide a practical size to dosage relationship. Preferably, the pharmaceutical carrier comprises from about 0.1% to 99% by weight of the total composition.

Animal feed compositions to which the carbonyldiphosphonates of this invention can be added generally include as feedstuffs a cellulosic roughage component such as hay, straw, cottonseed hulls, beet pulp, silage, ground corn cobs, corn stalks, etc. Protein-containing components such as whole grains, including corn, wheat, barley, oats, rye, millet and alfalfa; processed grains, including cottonseed meal, corn meal, soybean meal, linseed meal and other waste products from the oil expressing industry; animal protein including casein, gelatin, fish meal, and slaughterhouse wastes, are also required feedstuffs for a nutritionally balanced feed composition. Animal feed compositions can also contain natural oils, including animal fats, such as feed tallow, mutton tallow; fish oils, including eel, herring, menhaden, tuna and salmon oil; and whale oil. Vegetable oils such as soybean oil, sunflower oil, olive oil, safflower oil, corn oil, peanut oil, cottonseed oil, rice oil, millet oil, wheat germ oil and palm oil, can also be used.

In addition to the feedstuffs mentioned above, animal feed compositions can include supplemental sources of minerals, such as bone meal, salt, and the various trace minerals, such as salts of zinc, copper, manganese, magnesium, cobalt, iodine and iron. Antibiotics, steroids, anthelmintics and other medicants or growth stimulating substances can be incorporated in animal feeds. Various vitamins can be added to animal feed compositions to provide for deficiencies incident to the selection of other feed components. Other feedstuffs can be included such as casein, other milk by-products, and synthetic nitrogen sources such as urea.

The carbonyldiphosphonates can be incorporated in the total feed composition as described above or in intermediate feed concentrates or feed supplements which are adapted to be blended with the basic roughage and protein feedstuffs to prepare the final feed. In the feed industry the term "concentrate" is often used to denote a product which contains a relatively large quantity of one or more nutrients, such as high quality protein, minerals, vitamins and the like and which is adapted for addition to the basic feedstuffs to form a total or final feed. The term "supplement" is also used to denote a specific feedstuff or mixture thereof that is either added to or included in the concentrate portion of the total feed, or in the total feed itself. The carbonyldiphosphonates can be employed in accordance with this invention by incorporating same in feed supplements, concentrates or the total feed composition (all referred to hereinafter as "feed compositions"). For the purpose of this invention, the term "pharmaceutical carrier" is intended to encompass feed compositions.

Feed compositions containing a minor proportion of one or more of the carbonyldiphosphonates described herein incorporated in a major proportion of an animal foodstuff constitute a preferred embodiment of this invention inasmuch as they provide an effective and practical means of urolithiasis prophylaxis for large herds of animals, especially during periods of feed-lot maintenance or limited grazing. Urolithiasis prophylaxis can be achieved in grazing herds by incorporating the carbonyldiphosphonates in block salt.

The concentration of carbonyldiphosphonate in feed compositions will of course vary with the weight of the animal to be treated and the proportion of the total diet which the feed composition comprises. When herds of animals are to be treated, the level of carbonyldiphosphonate in the feed composition should be sufficient to provide the dosage specified herein based on the average feed consumption and weight of the animals. In any event, the carbonyldiphosphonates comprise a minor proportion of the total feed composition.

While it is not intended that this invention be limited by a particular theory of operation, in the case of those conditions which cause or result from deposition of calcium and phosphate anomalously in the body, it is believed that carbonyldiphosphonates interfere with the conversion of x-ray amorphous calcium phosphate to crystalline calcium hydroxylapatite and thus greatly reduce or prevent the formation of calcium phosphate deposits. Although certain inorganic phosphates also inhibit crystal growth, they are hydrolyzed soon after administration to the orthophosphate species which has no crystal growth inhibition properties and, in fact, can itself take part in hydroxylapatite formation. The carbonyldiphosphonates of this invention, on the other hand, do not hydrolyze to inactive forms and remain active after administration even to larger animals such as cattle.

CRYSTAL GROWTH INHIBITION DETERMINATION

The efficacy of carbonyldiphosphonates in inhibiting crystal growth was demonstrated by the Crystal Growth Inhibition Determination which was conducted as follows:

1 ml. of a 0.1 M stock solution of $NaH_2PO_4 \cdot H_2O$ was diluted with 22 ml. of distilled water. 1 ml. of an aqueous solution of tetrasodium carbonyldiphosphonate at a concentration sufficient to provide the desired ultimate concentration in the reaction mixture) was added to the diluted $NaH_2PO_4$ solution and the solution was adjusted to pH 7.4 with sodium hydroxide. To this solution was added 1 ml. of a 0.1 M solution of $CaCl_2 \cdot 2H_2O$ preadjusted to pH 7.4 with sodium hydroxide. This mixture was held at a constant pH 7.4 throughout the reaction period.

After a sufficient reaction time as determined by the operator, generally within 90 minutes, the solution was filtered through a 0.45 Millipore filter pad. The precipitate was air-dried and analyzed by x-ray diffraction. The solid calcium phosphate precipitated from the above-described solution without a carbonyldiphosphonate gives a typical hydroxylapatite pattern, while the calcium phosphate precipitated under the same conditions but in the presence of small amounts of this representative carbonyldiphosphonate was amorphous to x-rays.

Those compounds which are effective in inhibiting the growth of hydroxylapatite crystals at concentrations of less than $1.5 \times 10^{-3}$ M under the conditions of this test are found to inhibit anomalous mobilization and deposition of calcium phosphates in animal tissue, while several compounds outside the scope of this invention that have little or no effect in this test are ineffective in vivo.

When tested in the above-described manner carbonyldiphosphonate was found to inhibit crystal growth at a concentration of $2.3 \times 10^{-4}$ M. Similar values are obtained when the other carbonyldiphosphonates encompassed by this invention are tested in like manner.

The capacity of carbonyldiphosphonates to inhibit anomalous calcification is also demonstrated in vivo as follows:

This test is based on the observation that massive dosages of vitamin $D_3$ induces extensive calcification in the aorta of rats [see Gillman et al., *J. Exp. Path.*, 40:1 (1960)]. Female Wister rats each weighing 150 to 200 g. are randomly divided into a control group of 60 animals and test groups each containing 10 animals. The animals are kept in a thermostabilized room at 22° C. and receive a normal diet and tap water ad libitum throughout the test period. All of the animals are given daily doses of 75,000 units/kg. of vitamin $D_3$ via stomach tube for five days beginning on the third and ending on the seventh day of the test. Beginning on the first day (prior to the first dosage of vitamin $D_3$) until the conclusion of the test, the test groups of animals are administered specified dosages of carbonyldiphosphonates, orally by stomach tube or subcutaneously, respectively, once per day. In each case the carbonyldiphosphonates are dissolved in 0.9% NaCl when given at the lower dosages, and in distilled water when given at higher dosages. The solution is adjusted to pH 7.4 and the amount of solution given is 2 ml./kg. of body weight. On the fifteenth day, the animals are sacrificed and their aortas are dissected and dried for 48 hours at 120° C. After determination of the dry weight, the aortas are ashed in a muffle oven at 800° C. for 6 hours. The residue is dissolved in 0.2 N HCl and the calcium is titrated with EDTA using calcichrome as an indicator in a titration photometer, all in accordance with the methods described by Irving, et al., *Proc. Soc. Exp. Biol. Med.*, 122, #3, 852 (1966).

The calcium values secured in this test reveal that carbonyldiphosphonates materially reduce Vitamin $D_3$-induced calcification in the aorta of rats.

EXAMPLE I

Capsules are prepared by conventional methods, comprised as follows:

| Ingredient | mg per capsule |
|---|---|
| Tetrasodium carbonyldiphosphonate | 700.00 |
| Starch | 55.60 |
| Sodium lauryl sulfate | 2.90 |

The above capsules administered orally twice daily substantially reduce bone decalcification in a patient weighing approximately 70 kilograms afflicted with osteoporosis. Similar results are attained when the tetrapotassium salt and the tetraammonium salt are employed in the above described capsule in place of the tetrasodium salt.

EXAMPLE II

Tablets are prepared by conventional methods, formulated as follows:

| Ingredient | mg per tablet |
|---|---|
| Disodium-dipotassium carbonyldiphosphonate | 250.00 |
| Lactose | 40.00 |
| Starch | 2.50 |
| Magnesium stearate | 1.00 |

When administered orally four times daily, the above composition significantly reduces the formation of renal calculi in a patient weighing approximately 50 kilograms, having a predisposition to such formation.

Similar results are achieved with tablets formulated as above but replacing disodium-dipotassium carbonyldiphosphonate with the tetra(triethanolammonium) carbonyldiphosphonate.

The lactose employed in this example is replaced by sucrose and the magnesium stearate by sodium carbonylmethylcellulose without affecting the desired properties of the tablet.

Solutions for parenteral administration are prepared by dissolving the following carbonyldiphosphonates in distilled water at the specified concentration.

| Ex. | Phosphonate | Conc. mg./ml. |
|---|---|---|
| III | Tetrapotassium carbonyldiphosphonate | 15.0 |
| IV | Tetra(diethanolammonium) carbonyldiphosphonate | 13.0 |

The solutions of the foregoing examples when administered by injection to animals in an amount sufficient to provide recommended dosage levels as hereinbefore specified substantially reduce pathological calcification and hard tissue demineralization. Preferably, the solutions are packaged in 2 ml. sealed ampules for single dosage hypodermic injections.

EXAMPLE V

A complete feed composition embodying the present invention is prepared by grinding and mixing the following:

| Component | Parts by Weight |
|---|---|
| Timothy hay | 960 |
| Dehydrated alfalfa | 40 |
| Yellow corn | 600 |
| Corn starch | 310 |
| Iodized salt | 10 |
| Bone meal | 20 |
| Sea salt | 1.3 |
| Soybean meal | 30 |
| Biuret | 28 |
| Tetrasodium carbonyldiphosphonate | .70 |

This composition is fed to 400 pound weanling steers at a rate of approximately 12 pounds per day. The average dosage of carbonyldiphosphonate effected in this manner is about 1.91 g. per day (10.5 mg./kg. dose). Animals placed on this feed experience a substantially lower incidence of urolithiasis than control animals receiving the same feed but without the carbonyldiphosphonate.

EXAMPLE VI

A supplementary feed concentrate is prepared by intimately admixing the following:

| Component | Parts by Weight |
|---|---|
| Biuret | 400 |
| Brewer's dried grains | 33 |
| Dehydrated alfalfa | 53 |
| Iodized salt | 10 |
| Tricalcium phosphate | 2.4 |
| Dipotassium disodium carbonyldiphosphonate | 1.6 |

This composition is suitable for mixing with silage, grain, hay, ground grain and the like for preparing total feed compositions for ruminant livestock. When fed as a supplement to legumes consumed by grazing weanling lambs at the rate of 0.25 pounds per day, this supplement greatly reduces the incidence of urolithiasis. The average dosage for a 40 pound lamb is 0.363 g. per day (or 20 mg./kg.).

What is claimed is:

1. A method for treating urolithiasis comprising administering to an animal afflicted therewith an effective but non-toxic amount of a pharmaceutically acceptable alkali metal, ammonium, or low molecular weight substituted ammonium carbonyldiphosphonate.

2. A method for treating arteriosclerosis comprising administering to an animal afflicted therewith an effective but non-toxic amount of a pharmaceutically acceptable alkali metal, ammonium, or low molecular weight substituted ammonium carbonyldiphosphonate.

* * * * *